United States Patent
Garssen et al.

(10) Patent No.: US 9,782,422 B2
(45) Date of Patent: Oct. 10, 2017

(54) TREATMENT OF CONDITIONS ASSOCIATED WITH MYCOTOXIN EXPOSURE

(71) Applicant: N.V. Nutricia, Zoetermeer (NL)

(72) Inventors: Johan Garssen, Utrecht (NL); Hermiena Christina Schoterman, Zutphen (NL); Johanna Fink-Gremmels, Utrecht (NL); Saskia Braber, Zeist (NL)

(73) Assignee: N.V. Nutricia, Zoetermeer (NL)

( * ) Notice: Subject to any disclaimer, the term of this patent is extended or adjusted under 35 U.S.C. 154(b) by 117 days.

(21) Appl. No.: 14/401,815

(22) PCT Filed: May 17, 2013

(86) PCT No.: PCT/NL2013/050366
§ 371 (c)(1),
(2) Date: Nov. 17, 2014

(87) PCT Pub. No.: WO2013/172714
PCT Pub. Date: Nov. 21, 2013

(65) Prior Publication Data
US 2015/0164931 A1    Jun. 18, 2015

(30) Foreign Application Priority Data
May 18, 2012 (WO) .................. PCT/EP2012/059266

(51) Int. Cl.
*A61K 31/702* (2006.01)
*A23L 33/00* (2016.01)
*A23L 33/21* (2016.01)

(52) U.S. Cl.
CPC ............ *A61K 31/702* (2013.01); *A23L 33/21* (2016.08); *A23L 33/40* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 6,045,834 A | 4/2000 | Howes et al. | |
| 2010/0189871 A1 | 7/2010 | Yu et al. | |
| 2012/0196811 A1* | 8/2012 | Dikovskiy | A61K 31/7016 514/22 |

FOREIGN PATENT DOCUMENTS

| | | |
|---|---|---|
| CN | 101940911 A | 12/2011 |
| WO | WO-2011/037495 A1 | 3/2011 |
| WO | WO-2011/037497 | 3/2011 |

OTHER PUBLICATIONS

Moro, G. et al "Dosage-related bifidogenic effects . . . " J. Ped. Gastroenterol. Nutr. (2002) vol. 34, pp. 291-295.*
Vos, A. et al "Dietary supplementation of neutral . . . " Ped. Allergy Immunol. (2007) vol. 18, pp. 304-312.*
Torres, D. et al "Galacto-oligosaccharides: production, properties . . . " Comp. Rev. Food Sci. Food Safety (2010) vol. 9, pp. 438-454.*
Bhat, R. et al "Mycotoxins in food and feed . . . " Comp. Rev. Food Sci. Food Safety (2010) vol. 9, pp. 57-81.*
Petska, J. "Deoxynivalenol: mechanism of action . . . " Arch. Toxicol. (2010) vol. 84, pp. 663-679.*
Torre, M. et al "Study of the interaction of calcium ions with lignin . . . " J. Agric. Food Chem. (1992) vol. 40, pp. 1762-1766.*
Bosscher, D. "Effect of thickening agents . . . " Nutrition (2001) vol. 17, pp. 614-617.*
Meissannier, G.M. et al., "Dietary glucomannan improves the vaccinal response in pigs exposed to alfatoxin B1 or T-2 toxin", World Mycotoxin Journal, vol. 2, No. 2, May 2009, pp. 161-172
Avantaggiato, G. et al., "Evaluation of the intestinal absorption of deoxynivalenol and nivalenol by an in vitro gastrointestinal model, and the binding efficacy of activated carbon and the other adsorbent materials", Food and Chemical Toxicology, vol. 42, 2004, pp. 817-824.
Awad, W. et al., "A nutritional approach for the management of deoxynivalenol (DON) toxicity in the gastrointestinal tract of growing chickens", Int. J. Mol. Sci., vol. 9, 2008, pp. 2505-2514.
International Preliminary Report on Patentability in International Appln. No. PCT/NL2013/050366 mailed Jul. 15, 2014.
International Search Report of PCT/NL2013/050366 mailed Jul. 15, 2013.
Maresca, M. et al., "The mycotoxin deoxynivalenol affects nutrient absorption in human intestinal epithelial cells", J. Nutr., vol. 132, 2002, pp. 2723-2731.
Shan et al., "Research progress on method of mycotoxin detoxification in feedstuffs", Feed Research, 2005, vol. 11, translation (6 pgs.).

* cited by examiner

*Primary Examiner* — Leigh C Maier
(74) *Attorney, Agent, or Firm* — Gilberto M. Villacorta; Sunit Talapatra; Foley & Lardner LLP

(57) ABSTRACT

We describe a composition comprising a non-digestible oligosaccharide for the treatment, prevention or alleviation of a trichothecene mycotoxin exposure associated condition. The non-digestible oligosaccharide may comprise a galactooligosaccharide and/or fructooligosaccharide. The non-digestible oligosaccharide may comprise a short chain galacto-oligosaccharide (scGOS) and/or short chain fructooligosaccharide (scFOS). The trichothecene mycotoxin exposure associated condition may be associated with exposure to deoxynivalenol.

18 Claims, 7 Drawing Sheets

TREATMENT OF CONDITIONS ASSOCIATED WITH MYCOTOXIN EXPOSURE

CROSS REFERENCE TO RELATED APPLICATIONS

The present application is a National Stage of International Application No. PCT/NL2013/050366, filed May 17, 2013, which claims priority to International Application No. PCT/EP2012/059266, filed May 18, 2012. The contents of these applications are herein incorporated by reference in their entirety.

FIELD

The present invention relates to the field of infant and/or toddler nutrition. In particular the present invention relates to a non-digestible oligosaccharide composition suitable for use in infant and/or toddler nutrition.

BACKGROUND

Mycotoxins are secondary metabolites produced by moulds and fungi contaminating cereal grains as well as forages, fruits, feed and food products as well as the environment (e.g., soil, water and air through aerosol acquired mycotoxicosis, etc.).

Mycotoxins may have dangerous effects on human and animal health. Of particular note are the trichothecene mycotoxins, which are a class of compounds produced by the species *Fusarium graminearum*. This large family of sesquiterpene epoxides are closely related and vary by the position and number of hydroxylations and substitutions of a basic chemical structure. The major trichothecene produced by *Fusarium graminearum* is deoxynivalenol (DON) also known as vomitoxin for its ability to induce vomiting. The impact of DON on nutrient absorption in human intestinal epithelial cells has been investigated in Maresca et al. "*The mycotoxin deoxynivalenol affects nutrient absorption in human intestinal epithelial cells*" J. Nutr. Vol. 132 (2002) 2723-2731, and in Avantaggiato et al. "*Evaluation of the intestinal absorption of deoxynivalenol and nivalenol by an in vitro gastrointestinal model, and the binding efficacy of activated carbon and other absorbent materials*" Food and Chemical Toxicology vol. 42 (2004) 817-824.

Mycotoxins can appear in the food chain as a result of fungal infection of plant products (e.g., forage, grain, plant protein, processed grain by-products, roughage and molasses products), and can either be eaten directly by humans, or introduced by contaminated grains, livestock or other animal feedstuff(s). Furthermore, mycotoxins greatly resist decomposition during digestion so they remain in the food chain in edible products (e.g., meat, fish, eggs and dairy products) or under the form of metabolites of the parent toxin ingested. Temperature treatments such as cooking and freezing are not adequate methods of decreasing the prevalence of mycotoxins.

Mycotoxin contamination is unavoidable, and in order to reduce the negative effects of mycotoxins, inorganic materials such as clays, bentonites and aluminosilicates, or activated charcoal, known for their adsorptive properties, were historically used in agriculture (e.g., admixed with animal feed and/or ingredients, encapsulated forms or as filter devices). Clays used in large quantities sequester some mycotoxins in fluids (e.g., in the gastrointestinal tract of the animal and/or humans) and minimize their toxic effects (See e.g., Ramos A. J., and Hernandez E., 1997. Animal Feed Science and Technology, 65: 197-206; Grant P. G., and Phillips T. D., 1998. Journal of Agricultural and Food Chemistry, 46: 599-605). As a biotoxin sorbent for feed, US 2010/189871 discloses a combination of clay and yeast manna oligosacccharide (MOS) which is an extract of yeast cell wall separated from *Saccharomyces cerevisiae*. The role of clay in US 2010/189871 is unmistakable.

However, clays hinder the absorption of many beneficial nutrients that are important to animals and humans such as vitamins, minerals and amino acids thereby decreasing the nutrient density of the diet. Moreover, clays are an inert material that must be used (e.g., fed to animals) in large quantities to have a beneficial effect (e.g., reduction of mycotoxin contamination). Furthermore, clays fed to animals in large quantities can have a negative effect on the environment when the clays are excreted from the animal. Other broad spectrum mycotoxin adsorbents, which lack specificity for specific mycotoxins, including the invention described in U.S. Pat. No. 6,045,834, have also been used.

WO 2011/037497 discloses veterinary pharmaceutical compositions comprising a hydrolyzed lignin and a prebiotic for treating diseases of the gastrointestinal tract and intoxications of diverse ethiology in poultry, and the list of diseases includes dyspepsia, gastroenteritis, enteritis, colitis, hepatitis and hepato-dystrophy.

Meissannier et al. "*Dietary glucomannan improves the vaccinal response in pigs exposed to aflatroxin B1 or T-2 toxin*" World Mycotoxin Journal Vol. 2, no. 2 (2009) 161-172 involves a study to investigate whether dietary supplementation with yeast-derived glucomannan protects pigs against the deleterious effects that exposure to aflatoxin B1 or T-2 toxin has on the vaccinal immune response and drug-metabolizing enzymes. As addressed in US 2010/189871, the limited water-solubility of glucomannans leads to its insufficient contact with mycotoxin and bad absorption effect to wide-spectrum moulds (mildew).

Awad et al. "A nutritional approach for the management of deoxynivalenol (DOM) toxicity in the gastrointestinal tract of growing chickens" Int. J. Mol. Sci. Vol. 9 (2008) 2505-2514 provides an in vitro study to evaluate the effect of inulin on the electrophysiological parameters in the presence and absence of the mycotoxin deoxynivalenol in the chicken gut. Insulins used in these studies are provided by Orafti and typically marketed having an average DP of higher than 10. While it finds the use of inulin offers a promising approach as shows improved glucose absorption in the presence of DON, it suggests further studies need to be done to extend its findings.

Thus, there exists a need for compositions and/or methods for reducing the detrimental effects and/or eliminating mycotoxin occurrence in feed and/or food chains, and/or at least to provide the public with a useful choice.

SUMMARY

According to a $1^{st}$ aspect of the present invention, we provide use of a non-digestible oligosaccharide in the preparation of a medicament for the treatment, prevention or alleviation of a trichothecene mycotoxin exposure associated condition in an individual. There is provided, according to a $2^{nd}$ aspect of the present invention, a composition comprising a non-digestible oligosaccharide for the treatment, prevention or alleviation of a trichothecene mycotoxin exposure associated condition.

The trichothecene mycotoxin may comprise deoxynivalenol.

The non-digestible oligosaccharide may comprise a galacto-oligosaccharide and/or a fructo-oligosaccharide.

The trichothecene mycotoxin exposure associated condition may comprise a condition that has resulted from exposure to a trichothecene mycotoxin.

The trichothecene mycotoxin exposure associated condition may comprise mycotoxicoses. It may comprise listlessness, inactivity, fatigue, chills, dizziness, headache, nausea, sore throat, coughing, vomiting, reduced food or feed intake, slowed weight gain, food or feed refusal, weight loss, diarrhoea, blood in the stool, rectal haemorrhaging, gastrointestinal tract necrosis, bone marrow necrosis, destruction of bone marrow, lymphoid tissue necrosis, severe dermal necrosis, changes in blood parameters, modulation of serum immunoglobulin levels, abdominal pain, throat irritation, gastrointestinal disturbances, gastrointestinal inflammation, dermal irritation, abortion, anaemia, leukopenia, cytotoxicity, immunosuppression, necrotic lesions in mouth parts, erosion of mucosal epithelium of the stomach, erosion of mucosal epithelium of the small intestine, haemorrhage, severe gastroenteritis, death, massive haemorrhaging in the small intestine, pathological degeneration of bone marrow cells, pathological degeneration of lymph node cells, pathological degeneration of intestine cells, inhibition of DNA synthesis, inhibition of protein synthesis and alimentary toxic aleukia (ATA).

The medicament or composition may comprise a food or beverage comprising the non-digestible oligosaccharide and at least one cereal, vegetable, fruit, animal milk, or animal protein.

The individual may be a human baby. It may be an infant. It may be a toddler. It may be a young child. It may be a weaning infant or a weaning toddler. The individual may be anywhere between 12 to 60 months old, suitably anywhere between 12 and 36 months old.

We provide, according to a $3^{rd}$ aspect of the present invention, a method of treating, preventing or alleviating a trichothecene mycotoxin exposure associated condition in a cell, tissue or organ. The method may comprise exposing the cell, tissue or organ to a composition comprising a non-digestible oligosaccharide.

As a $4^{th}$ aspect of the present invention, there is provided use of a non-digestible oligosaccharide for the ex-vivo treatment, prevention or alleviation of a trichothecene mycotoxin exposure associated condition in a cell, tissue or organ.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

LIST OF EMBODIMENTS

Figure 1:
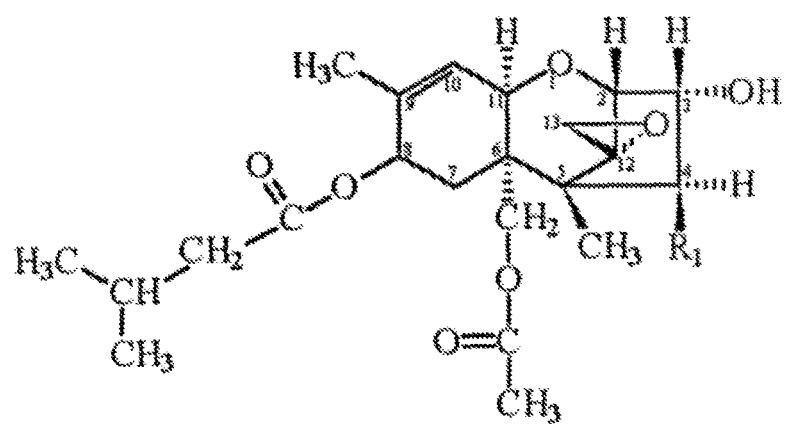
FIG. 1 shows the chemical structure of a Group A trichothecene mycotoxin.

1. Use of a non-digestible oligosaccharide in the preparation of a composition for the treatment, prevention or alleviation of a trichothecene mycotoxin exposure associated condition in an individual.
2. Use of a non-digestible oligosaccharide for the ex-vivo treatment, prevention or alleviation of a trichothecene mycotoxin exposure associated condition in a cell, tissue or organ.

3. A composition comprising a non-digestible oligosaccharide for use in the treatment, prevention or alleviation of a trichothecene mycotoxin exposure associated condition in an individual.
4. Use according to c1 or 2, or a composition for use according to embodiment 3, in which the trichothecene mycotoxin comprises deoxynivalenol.
5. Use or a composition for use according to any preceding embodiment, in which the non-digestible oligosaccharide has a degree of polymerisation (DP) of 2-10.
6. Use or a composition for use according to any preceding embodiment, in which the non-digestible oligosaccharide comprises a galactooligosaccharide and/or a fructooligosaccharide.
7. Use or a composition for use according to embodiment 5 or 6, in which the non-digestible oligosaccharide comprises a short-chain galactooligosaccharide and/or a short-chain fructooligosaccharide.
8. Use or a composition for use according to embodiment 5 or 6, in which the non-digestible oligosaccharide comprises a transgalacto-oligosaccharide.
9. Use or a composition for use according to embodiment 8, in which the non-digestible oligosaccharide composition comprises a short chain galacto-oligosaccharide (scGOS).
10. Use or a composition for use according to any preceding embodiment, in which the composition comprises a food or beverage comprising the non-digestible oligosaccharide and at least one cereal, vegetable, fruit, animal milk, or animal protein.
11. Use according to embodiment 1 or a composition for use according to embodiment 3, in which the individual is a human baby, infant, toddler, or young child, such as a weaning infant or a weaning toddler, preferably a toddler between 12 to 36 months old.
12. A method of treating, preventing or alleviating a trichothecene mycotoxin exposure associated condition in a cell, tissue or organ, the method comprising exposing the cell, tissue or organ to a composition comprising a non-digestible oligosaccharide.
13. The method according to embodiment 12, wherein the non-digestible oligosaccharide has a degree of polymerisation (DP) of 2-10.
14. The method according to embodiment 12 or 13, wherein the non-digestible oligosaccharide comprises a galactooligosaccharide and/or a fructooligosaccharide.
15. The method according to any of embodiments 12-14, in which the trichothecene mycotoxin comprises deoxynivalenol.

DETAILED DESCRIPTION

Non-Digestible Oligosaccharide Compositions

We have therefore surprisingly demonstrated, that it is possible to treat, prevent or alleviate one or more conditions associated with exposure to trichothecene mycotoxins (in an individual, tissue, organ or cell).

We demonstrate that this may be achieved through administration of a composition comprising a non-digestible oligosaccharide. Such a non-digestible oligosaccharide composition may be administered to reduce or alleviate any of the symptoms or conditions associated with exposure to trichothecene mycotoxins in an individual, such as an infant or a toddler.

The composition may comprise a non-digestible oligosaccharide and may comprise a water soluble non-digestible oligosaccharide composition, such as a galacto-oligosaccharide and/or a fructo-oligosaccharide, preferably at least a galacto-oligosaccharide. We show in the Examples that a galacto-oligosaccharide or a fructo-oligosaccharide composition is capable of reversing or alleviating the effects of exposure of a cell to a trichothecene mycotoxin such as deoxynivalenol.

In general, the compositions and methods described here make use of a non-digestible oligosaccharide composition, which is described in detail below. Such a composition may comprise a non-digestible oligosaccharide such as a galacto-oligosaccharide or a fructo-oligosaccharide, preferably at least a galacto-oligosaccharide.

Uses of Non-Digestible Oligosaccharide Compositions

As noted above, the Examples demonstrate that such a non-digestible oligosaccharide composition is capable of preventing, alleviating or treating a deleterious effect of a trichothecene mycotoxin such as deoxynivalenol on a cell or tissue. Throughout the description, with "non-digestible oligosaccharide composition" it is understood a composition comprising a non-digestible oligosaccharide.

Trichothecene mycotoxins such as deoxynivalenol are known to cause a number of severe effects on individuals unfortunate to ingest them or to be exposed to them. A detailed description of conditions associated with exposure to trichothecene mycotoxins is set out below.

Accordingly, we provide for the use of a non-digestible oligosaccharide composition such as an scGOS composition or scFOS composition, preferably a scGOS composition, for the treatment, prophylaxis, prevention or alleviation of mycotoxicoses, listlessness, inactivity, fatigue, chills, dizziness, headache, nausea, sore throat, coughing, vomiting associated with exposure to a trichothecene mycotoxin such as deoxynivalenol.

We further provide for the use of a non-digestible oligosaccharide composition such as scGOS composition or scFOS composition, preferably a scGOS composition, for the treatment, prophylaxis, prevention or alleviation of reduced food or feed intake, slowed weight gain, food or feed refusal or weight loss associated with exposure to a trichothecene mycotoxin such as deoxynivalenol.

We further provide for the use of a non-digestible oligosaccharide composition such as a galacto-oligosaccharide composition or fructo-oligosaccharide composition, preferably a GOS composition, for the treatment, prophylaxis, prevention or alleviation of diarrhoea, blood in the stool, rectal haemorrhaging, gastrointestinal tract necrosis, abdominal pain, throat irritation, necrotic lesions in mouth parts, gastrointestinal disturbances, gastrointestinal inflammation, erosion of mucosal epithelium of the stomach, erosion of mucosal epithelium of the small intestine, haemorrhage, severe gastroenteritis, massive haemorrhaging in the small intestine or death associated with exposure to a trichothecene mycotoxin such as deoxynivalenol.

We further provide for the use of a non-digestible oligosaccharide composition such as a galacto-oligosaccharide composition or fructo-oligosaccharide composition, preferably a GOS composition, for the treatment, prophylaxis, prevention or alleviation of dermal irritation, abortion, anaemia, leukopenia, cytotoxicity, immunosuppression, bone marrow necrosis, destruction of bone marrow, lymphoid tissue necrosis, severe dermal necrosis, changes in blood parameters, modulation of serum immunoglobulin levels associated with exposure to a trichothecene mycotoxin such as deoxynivalenol.

We further provide for the use of a non-digestible oligosaccharide composition such as a galacto-oligosaccharide composition or fructo-oligosaccharide composition, preferably a GOS composition, for the treatment, prophylaxis, prevention or alleviation of pathological degeneration of bone marrow cells, pathological degeneration of lymph node cells, pathological degeneration of intestine cells, inhibition of DNA synthesis, inhibition of protein synthesis and alimentary toxic aleukia (ATA) associated with exposure to a trichothecene mycotoxin such as deoxynivalenol.

Such effects may be in vitro or ex vivo and may be experienced by cells, tissues, organs or individuals.

For this purpose, a number of criteria may be designated, which reflect the progress of treatment or prophylaxis or the well-being of the individual. Useful criteria in the case of the conditions described above may include for example any of the symptoms set out above in the individual, whether measured quantitatively or qualitatively (e.g., by questionnaires) as known in the art. Other indications may reflect the amount of vomiting, etc.

Thus, as an example, a treated individual may show a decrease in such a symptom as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in one or more symptoms, compared to an individual who has not been treated.

For example, a patient disease may be defined as being "treated" if a condition associated with the disease is significantly inhibited (i.e., by 50% or more) relative to controls. The inhibition may be by at least 75% relative to controls, such as by 90%, by 95% or 100% relative to controls. By the term "treatment" we mean to also include prophylaxis, prevention (including reducing the risk of occurrence), reduction or alleviation of any of the conditions or symptoms specified and/or the severity of any of the conditions or symptoms specified.

The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a substance that will elicit the biological or medical response of a tissue, a system, animal or human that is being sought by a researcher, veterinarian, medical doctor or other clinician. The term also encompasses the amount of a substance that will prevent or reduce the risk of occurrence of the biological or medical event that is sought to be prevented in a tissue, a system, animal or human by a researcher, veterinarian, medical doctor or other clinician.

Cellular, Tissue and Organ Conditions

It should be understood that the non-digestible oligosaccharide composition described here may be used to treat, alleviate and prevent any symptoms or conditions associated with exposure of an individual to trichothecene mycotoxin—as well as any symptoms or conditions associated with exposure of cells, tissues, or organs to trichothecene mycotoxin. Accordingly, the terms "treat", "alleviate" and "prevent" should be construed accordingly to refer to any reduction of the cellular, tissue or organ effects caused by or associated with exposure of the cells, tissues, or organs, as they may be, to trichothecene mycotoxin such as deoxynivalenol.

For example, it is seen from the Examples that exposure of a cell to a trichothecene mycotoxin such as deoxynivalenol decreases the transepithelial electrical resistance (TEER) of cells. Accordingly, a non-digestible oligosaccharide composition such as a scGOS or scFOS composition may be used to increase the transepithelial electrical resistance (TEER) of a cell, where the TEER of the cell has been reduced as a result of exposure to a trichothecene mycotoxin such as deoxynivalenol.

The Examples show that exposure of a cell to a trichothecene mycotoxin such as deoxynivalenol increases the luciferase yellow (LY) permeability of a cell. Accordingly, a non-digestible oligosaccharide composition such as a scGOS composition may be used to decrease the luciferase yellow (LY) permeability of a cell, where the LY permeability of the cell has been increased as a result of exposure to a trichothecene mycotoxin such as deoxynivalenol.

The Examples show that exposure of a cell to a trichothecene mycotoxin such as deoxynivalenol reduces the tight junction protein expression by a cell. Accordingly, a nondigestible oligosaccharide composition such as a scGOS composition may be used to increase the tight junction protein expression by a cell, where the tight junction protein expression of the cell has been decreased as a result of exposure to a trichothecene mycotoxin such as deoxynivalenol.

The Examples show that exposure of a cell to a trichothecene mycotoxin such as deoxynivalenol increases cytokine release by a cell. Accordingly, a non-digestible oligosaccharide composition such as a scGOS composition may be used to decrease cytokine release by a cell, where the cytokine release of the cell has increased as a result of exposure to a trichothecene mycotoxin such as deoxynivalenol.

The Examples show that exposure of a cell to a trichothecene mycotoxin such as deoxynivalenol increases intracellular inflammatory cascades (NF-κB) of cells. Accordingly, a non-digestible oligosaccharide composition such as a scGOS composition may be used to decrease intracellular inflammatory cascades (NF-κB) of a cell, where the intracellular inflammatory cascades have been increased as a result of exposure to a trichothecene mycotoxin such as deoxynivalenol.

The Examples show that exposure of a cell to a trichothecene mycotoxin such as deoxynivalenol increases galectin expression and release by a cell. Accordingly, a nondigestible oligosaccharide composition such as a scGOS composition may be used to decrease galectin expression and release by a cell, where the galectin expression and release has been increased as a result of exposure to a trichothecene mycotoxin such as deoxynivalenol.

The Examples show that exposure of a cell to a trichothecene mycotoxin such as deoxynivalenol decreases cell viability of a cell. Accordingly, a non-digestible oligosaccharide composition such as a scGOS composition may be used to increase the cell viability of a cell, where the cell viability has been decreased as a result of exposure to a trichothecene mycotoxin such as deoxynivalenol.

Assays to measure the effect of trichothecene mycotoxins such as deoxynivalenol on these cellular parameters, as well as the preventative or restorative effect of non-digestible oligosaccharide compositions on these parameters, are well known in the art.

For example, cell viability and other assays are described in detail in Riss and Moravec 2004, *Use of Multiple Assay Endpoints to Investigate the Effects of Incubation Time, Dose of Toxin, and Plating Density in Cell-Based Cytotoxicity Assays*, Assay and Drug Development Technologies, 2, 51-62.

Assays for galectin production by intestinal epithelial cells are described in detail in Kivit et al 2011, *Glycan recognition at the interface of the intestinal immune system: target for immune modulation via dietary components*, Eur J Pharmacol. 2011; 668 Suppl 1:S124-32.

Assays describing the suitability of Caco-2 cells as standardised permeability-screening assay are described in detail in Alsenz and Haenel 2003, *Development of a 7-Day, 96-Well Caco-2 Permeability Assay with High-Throughput Direct UV Compound Analysis*, Pharmaceutical Research, Vol. 20, No. 12.

Trichothecene Mycotoxin Exposure Associated Condition

We describe the use of a composition comprising a non-digestible oligosaccharide in the treatment, prevention or alleviation of a trichothecene mycotoxin exposure associated condition. The composition may be used to treat, prevent or alleviate such a condition in an individual. It may also be used to treat, prevent or alleviate such a condition in an organ, tissue or cell, as the case may be.

Where the term "trichothecene mycotoxin exposure associated condition" is used in this document, this should be considered as referring to a condition caused by or associated with exposure of an individual, organ, tissue or cell (as the case may be) to a trichothecene mycotoxin.

Trichothecene mycotoxins are described in further detail below. A trichothecene mycotoxin exposure associated condition may comprise a deoxynivalenol exposure related condition, as set out for trichothecene mycotoxin exposure associated conditions.

The trichothecene mycotoxin exposure associated condition may comprise a gastrointestinal condition. Accordingly, the composition comprising a non-digestible oligosaccharide composition may be used to treat, prevent or alleviate a gastrointestinal condition.

The gastrointestinal condition may comprise an impaired intestine. The gastrointestinal condition may comprise a compromised epithelial lining of an intestine of an individual. The gastrointestinal condition may comprise an impaired intestinal wall barrier, impaired intestinal function, impaired intestinal barrier permeability, and/or an intestinal lesion.

The composition comprising a non-digestible oligosaccharide composition may be used for strengthening, restoring or improving intestinal wall barrier in an individual, such as when this has been compromised by exposure to a trichothecene mycotoxin.

The composition comprising a non-digestible oligosaccharide composition may be used for strengthening, restoring or improving intestinal function in an individual, such as when this has been compromised by exposure to a trichothecene mycotoxin.

The composition comprising a non-digestible oligosaccharide composition may be used for decreasing, restoring or improving intestinal barrier permeability in an individual, such as when this has been compromised by exposure to a trichothecene mycotoxin.

The composition comprising a non-digestible oligosaccharide composition may be used for stimulating maturation of the intestinal barrier in an individual, such as when this has been compromised by exposure to a trichothecene mycotoxin.

The composition comprising a non-digestible oligosaccharide composition may be used for preventing or treating an intestinal lesion in an individual, such as when this has been compromised by exposure to a trichothecene mycotoxin.

The trichothecene mycotoxin exposure associated condition may comprise an immunological condition. Accordingly, the composition comprising a non-digestible oligosaccharide composition may be used to treat, prevent or alleviate an immunological condition.

The immunological condition may comprise an infection, an increased susceptibility to infections, or an inflammatory response.

The composition comprising a non-digestible oligosaccharide composition may be used for strengthening, restoring or improving the immune system in an individual, such as when this has been compromised by exposure to a trichothecene mycotoxin.

The composition comprising a non-digestible oligosaccharide composition may be used for strengthening, restoring or improving the immune function in an individual, such as when this has been compromised by exposure to a trichothecene mycotoxin.

Trichothecene mycotoxin exposure associated conditions may include any one or more of the following: listlessness, inactivity, fatigue, chills, dizziness, headache, nausea, sore throat, coughing, vomiting, reduced food or feed intake, slowed weight gain, food or feed refusal, weight loss, diarrhoea, blood in the stool, rectal haemorrhaging, gastrointestinal tract necrosis, bone marrow necrosis, destruction of bone marrow, lymphoid tissue necrosis, severe dermal necrosis, changes in blood parameters, modulation of serum immunoglobulin levels, abdominal pain, throat irritation, gastrointestinal disturbances, gastrointestinal inflammation, dermal irritation, abortion, anaemia, leukopenia, cytotoxicity, immunosuppression, necrotic lesions in mouth parts, erosion of mucosal epithelium of the stomach, erosion of mucosal epithelium of the small intestine, haemorrhage, severe gastroenteritis, death, massive haemorrhaging in the small intestine, pathological degeneration of bone marrow cells, pathological degeneration of lymph node cells, pathological degeneration of intestine cells, inhibition of DNA synthesis, inhibition of protein synthesis and alimentary toxic aleukia (ATA).

The individual may comprise any human or animal, such as a mammal. The individual may comprise an adult or a child. He or she may comprise an infant or a young child. The individual may be being breast fed, or may be in the process of weaning.

Non-Digestible Oligosaccharide Composition

We describe the use of a composition comprising a non-digestible oligosaccharide in the treatment, prevention or alleviation of a trichothecene mycotoxin exposure associated condition such as a deoxynivalenol exposure associated condition.

The non-digestible oligosaccharide may be such that it does not comprise an acidic oligosaccharide. The non-digestible oligosaccharide may comprise a non-acidic oligosaccharide. In some embodiments, the non-digestible oligosaccharide comprises a neutral non-digestible oligosaccharide.

The non-digestible oligosaccharide may be water-soluble, as determined according to the method disclosed in L. Prosky et al, J. Assoc. Anal. Chem 71: 1017-1023, 1988.

The non-digestible oligosaccharide may comprise an oligosaccharide with a degree of polymerisation (DP) of 2 to 200. The non-digestible oligosaccharide is preferably an oligosaccharide having a degree of polymerisation (DP) of 2 to 60, more preferably 2-40, even more preferably 2-20, most preferably 2-10, particularly 2-8, 2-7, 2-6, 3-6, 3-5. The average DP of the non-digestible oligosaccharide may be below 100, such as below 50, such as below 20, such as below 10. The non-digestible oligosaccharide may have an average DP of 2-10, such as 2-8, 3-7, 3-5, and any other range within these parameters. In a particularly preferred embodiment, the non-digestible oligosaccharide is a galactooligosaccharide or a fructooligosaccharide, or a mixture thereof, having a DP of 2-10, such as 2-8, 2-7, 2-6, 3-6, 3-5; and/or having an average DP 2-10, such as 2-8, 3-7, 3-5. In the context of the invention, these may be addressed as short chain GOS ('scGOS') and short chain FOS ('scFOS'), respectively. In one embodiment, a scGOS is particularly preferred.

As used in this document, the term "degree of polymerisation" or "DP" is intended to refer to the total number of saccharide units in an oligo- or polysaccharide chain. The "average DP" is intended to refer to the average DP of oligosaccharides or polysaccharide chains in a composition, without taking possible mono- or disaccharides into account (which may be removed if present).

The non-digestible oligosaccharide may be one that is not digested in the intestine by the action of digestive enzymes present in the human upper digestive tract (small intestine and stomach). The non-digestible oligosaccharide may be fermented by the human intestinal microbiota. For example, glucose, fructose, galactose, sucrose, lactose, maltose and the maltodextrins are considered digestible. The oligosaccharide raw materials may comprise monosaccharides such as glucose, fructose, fucose, galactose, rhamnose, xylose, glucuronic acid, GalNac etc., but these are not part of the non-digestible oligosaccharides as used in the present description.

The composition comprising a non-digestible oligosaccharide (and the associated methods of using the composition as described herein) may include a mixture of non-digestible oligosaccharides. The non-digestible oligosaccharide may be selected from the group consisting of galacto-oligosaccharide, such as transgalacto-oligosaccharide, xylooligosaccharide, arabino-oligosaccharide, arabinogalacto-oligosaccharide, glucooligosaccharide, such as gentio-oligosaccharide and cyclodextrin, glucomanno-oligosaccharide, galactomanno-oligosaccharide, mannan-oligosaccharide, chito-oligosaccharide, fructo-oligosaccharide, such as inulin, non-digestible dextrin, uronic acid oligosaccharide, sialyloligosaccharide, such as 3-SL, 6-SL, LSTa.b.c, DSLNT, S-LNH, DSLNH, and fuco-oligosaccharide, such as (un)sulphated fucoidan OS, 2-FL, 3-FL, LNFP I, II, III, V, LNnFPI, LNDH, and mixtures thereof. The non-digestible oligosaccharide may particularly be selected from the group consisting of galacto-oligosaccharide, such as transgalacto-oligosaccharide, and fructo-oligosaccharide, particularly scGOS and/or scFOS. In a most preferred embodiment, the non-digestible oligosaccharide comprises at least galacto-oligosaccharide, particularly scGOS.

Although the composition may comprise only a single non-digestible oligosaccharide, we also describe compositions with two different non-digestible oligosaccharides, i.e. non-digestible oligosaccharide A and non-digestible oligosaccharide B. Non-digestible oligosaccharide A and non-digestible oligosaccharide B may have a different type of glycosidic linkage, a different degree of polymerisation and/or a different monosaccharide composition.

The non-digestible oligosaccharide may comprise a particular glycosidic linkage diversity. The term "glycosidic linkage" may be used in this document to refer to a C—O—C linkage formed between the rings of two cyclic monosaccharides by the elimination of water. Glycosidic linkages differ in that they covalently bind carbon atoms in the monosaccharide units at differently numbered positions, and/or that they form α-(alpha) or β-(beta) bonds. Examples of different glycosidic linkages occurring in non-digestible saccharides are β(1,3), α(1,4), β(2,1), α(1,2), and β(1,4) linkages. The glycosidic linkages in the non-digestible oligosaccharide may comprise at least 40% β(1,4) and/or β(1,6) glycosidic linkages, such as at least 75%.

For example, at least 60%, such as at least 75% such as 90%, such as 98% of the total monosaccharide units of the non-digestible oligosaccharide, may comprise monosaccharides selected from the group consisting of galactose (gal), fructose (fru) and glucose (glu) monosaccharides.

The non-digestible oligosaccharide may comprise an oligosaccharide selected from the group consisting of β-galacto-oligosaccharide, α-galacto-oligosaccharide, and galactan. β-galacto-oligosaccharide is also sometimes referred to as transgalacto-oligosaccharide. For example, the non-digestible oligosaccharide may comprise galacto-oligosaccharides with β(1,4), β(1,3) and/or β(1,6) glycosidic bonds and a terminal glucose. Transgalactooligosaccharide is for example available under the trade name Vivinal®GOS (Borculo Domo Ingredients, Zwolle, Netherlands), Bi2muno (Clasado), Cup-oligo (Nissin Sugar) and Oligomate55 (Yakult). Fructooligosaccharides may be inulin hydrolyzate products, preferably with a DP and/or average DP within the aforementioned (sub-)ranges; such FOS products are for instance commercially available as Raftilose P95 (Orafti) or with Cosucra.

For example, a transgalacto-oligosaccharide with an average DP below 10, such as 6 may be used as the non-digestible oligosaccharide.

The galacto-oligosaccharide (GOS) may comprise a short chain galactooligosaccharide (scGOS).

The non-digestible oligosaccharide may be present in the composition at any suitable concentration, preferably in a therapeutically effective amount or "amount effective for treating" as defined above. For example, where the composition comprises a liquid, such as made-up formula milk or a made-up growing up milk, the non-digestible oligosaccharide may be present at for example, between 0.01 g/100 ml to 10 g/100 ml (0.1 to 100 g/l), 0.05 g/100 ml to 5.0 g/100 ml, 0.10 g/100 ml to 2.0 g/100 ml, 0.20 g/100 ml to 1.0 g/100 ml or 0.10 g/100 ml to 1.0 g/100 ml, etc.

Compositions containing fructo-oligosaccharide(s) and/or galacto-oligosaccharide(s) are described in detail in WO 2000/08948 (and English language equivalents such as AU 766924), WO 2005/039597 and WO 2005/110121, each of which is herein incorporated by reference.

Trichothecene Mycotoxins

The '12,13-epoxytrichothecenes' (also known as "trichothecene mycotoxins" and "trichothecenes") are a large group of chemicals characterised by a double bond between C9 and C10 and an epoxy ring at the C12-C13 position in the chemical structure.

The trichothecene mycotoxins are a group of related and biologically active mycotoxins often wrongly referred to as the *Fusarium* toxins as several other fungal genera including *Trichoderma, Stachybotrys, Verticimonosporium, Cephalosporium* and *Myrothecium* can also produce them. Although the number of compounds of this type runs into the hundreds, only a few have been shown to be agriculturally important. However the fusaria are by far the most important mycotoxin-producing species occurring widely in field crops with more than 20 species of *Fusarium*, including *F. poae, F. sporotrichioides, F. moniliforme, F. culmorum*, and *F. graminearum* among the most important trichothecene producers.

Figure 2:
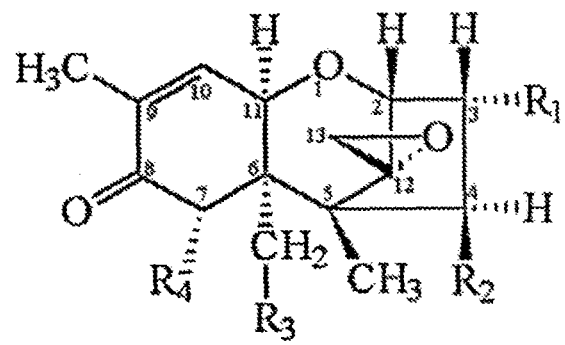
FIG. 2 shows the chemical structure of a Type B or Group B trichothecene mycotoxin.

Trichothecene mycotoxins are often classified as Group A and Group B compounds (also known as Type A and Type B) depending on whether they have a side chain on the C7 atom. The chemical structure of trichothecenes is shown in FIGS. 1 and 2. FIG. 1 shows the structure of a "Type A or Group A" trichothecene (Formula I), while FIG. 2 shows the structure of a "Type B or Group B" trichothecene (Formula II).

The most commonly reported Group A trichothecenes include, T-2 toxin, HT-2 toxin, neosolaniol, monoacetoxy scirpenol and diacetoxyscirpenol. Common group B trichothecenes are deoxynivalenol, nivalenol, 3- and 15-acetoxynivalenol and fusarenon X (a separate fact sheet is devoted to deoxynivalenol). In addition to producing mycotoxins these fungi include important plant pathogens that cause a number of serious diseases in growing crops.

Deoxynivalenol is a "Type B" or "Group B" trichothecene mycotoxin (in Formula II, shown in FIG. 2, $R_1$=OH, $R_2$=H, $R_3$=OH, $R_4$=OH in deoxynivalenol).

Another group of trichothecenes which are generally more acutely toxic than T-2 toxin are known as the macrocyclic trichothecenes produced by mould species such as *Stachybotrys atra*. These include the satratoxins, verrucarins and roridins.

Chemical and Physical Properties

All trichothecenes containing an ester group are hydrolysed to their respective parent alcohols when treated with alkali. A dilute solution of potassium carbonate, sodium hydroxide or ammonium hydroxide hydrolyses T-2 toxin and neosolaniol to T-2 tetraol and diacetoxyand monoacetoxy-scirpenol to scirpentriol. Many of the alcohols are unaffected, even by hot dilute alkali. Trichothecenes are thus chemically stable and can persist for long periods once formed. Prolonged boiling in water or under highly acidic conditions causes a skeletal rearrangement due to opening of the epoxide ring. Owing to the hindered nature of the epoxide and stability of the ring system, reactions of the trichothecenes usually proceed in a manner predictable from sound chemical principles, e.g. primary and secondary hydroxyl groups are easily oxidised to the aldehyde and ketone derivatives by reagents such as $CrO_3$—$H_2SO_4$ in acetone, $CrO_3$-pyridine and $CrO_3$-acetic acid.

Group A trichothecenes, T-2 toxin, HT-2 toxin, neosolaniol, monoacetoxy scirpenol and diacetoxyscirpenol are highly soluble in ethyl acetate, acetone, chloroform, methylene chloride and diethyl ether. The Group B trichothecenes, deoxynivalenol (commonly called 'DON' or 'vomitoxin'), nivalenol, 3-acetyldeoxynivalenol, 15-acetyldeoxynivalenol, fusarenone-X, scirpentriol and T-2 tetraol are highly hydroxylated and relatively polar being soluble in methanol, acetonitrile and ethanol.

Toxicity and Importance

When given orally or by intraperitoneal injection, the trichothecenes are acutely toxic at low concentrations although the acute toxicity varies considerably as shown. T-2 toxin and the macrocyclic mycotoxins are far more toxic than deoxynivalenol, but occur less commonly in agricultural products. Acute trichothecene toxicity is characterised by gastrointestinal disturbances, such as vomiting, diarrhoea and inflammation, dermal irritation, feed refusal, abortion, anaemia and leukopenia. This group of toxins are acutely cytotoxic and strongly immunosuppresive.

LD50 values for mice (intraperitoneal route) for some trichothecenes

| Trichothecene | LD50 (mg/kg bw) |
|---|---|
| deoxynivalenol | 70 |
| diacetoxyscirpenol | 23 |
| Neosolaniol | 14.5 |
| HT-2 toxin | 9.0 |
| T-2 toxin | 5.2 |
| nivalenol | 4.1 |
| verrucarin A | 0.5 |

Dosed animals become listless or inactive and develop diarrhoea and rectal haemorrhaging. Necrotic lesions may develop in the mouth parts. The mucosal epithelium of the stomach and small intestine erodes, accompanied by haemorrhage, which may develop, into severe gastroenteritis, followed by death. In larger animals, massive haemorrhages develop in the small intestine. The cells of the bone marrow, lymph nodes and intestines undergo a pathological degeneration. The trichothecenes have not been shown to be mutagenic or carcinogenic, but do inhibit DNA and protein synthesis.

A characteristic of a number of the trichothecenes is to cause vomiting and this may limit the amount of food ingested by livestock. For example, pigs are very sensitive to the presence of deoxynivalenol and will reject contaminated feed effectively limiting any further toxic effects. However, many compounds of this group are immunosuppresive in low concentrations and this may be more important than their acute toxicities. Because of the number of closely related metabolites likely to occur in combination in foods or animal feeds, the toxicology is complex with both synergistic and antagonistic effects observed.

Alimentary toxic aleukia (ATA) is the most well recognised human trichothecenemycotoxicosis. T-2 toxin is thought to have contributed to the epidemiology of alimentary toxic aleukia in Russia last century, which was responsible for widespread disease and many deaths. Continuous exposure to trichothecenes results in skin rashes, which may proceed to necrotic lesions. Many outbreaks of acute human diseases involving nausea, vomiting, gastrointestinal upset, dizziness, diarrhoea and headache have occurred particularly in Asia and these outbreaks have been attributed to the consumption of *Fusarium*-contaminated grain. High concentrations of deoxynivalenol have been detected in some samples from such outbreaks.

Products Affected and Natural Occurrence

Surveys have shown that trichothecenes occur in cereal grains such as wheat, barley, maize, oats, rice, soya beans and in derived products such as breakfast cereals and beer. There are also reports of occurrences in other food commodities including sorghum, potatoes, bananas, mustard seed, groundnuts, mangoes, sunflower seeds and cassava. Past surveillance of cereals commonly targeted deoxynivalenol only although other trichothecenes are highly likely to be present and the recent trend is to screen for the range of related compounds that may be expected to occur.

Satratoxins, verrucarins and roridins and may be produced in hay and straw stored under unsatisfactory conditions and may cause symptoms including decreased performance in race horses, haemorrhaging and death, particularly in equines. However, there is little evidence that these compounds occur in human food although the presence of macrocyclic trichothecenes in air-borne fungal spores may contribute to some forms of 'sick building' syndrome.

Sampling and Analysis

Since the trichothecenes are a group of closely related compounds, physicochemical analytical methods are usually intended to determine more than one single trichothecene. Analytical procedures differ in extraction, clean up and determination steps, depending on which group of trichothecenes is to be analysed. Detailed information on analysis including the extraction solvents, cleanup methods and detection systems used is provided in the analytical series of fact sheets.

Most trichothecenes with the exception of some of the macrocyclics such as roridin A and verrucarin, possess little absorption in the UV, other than end absorption. Thus the original methods developed based on TLC were insensitive and non-specific requiring a range of derivatisation reagents such as concentrated $H_2SO_4$ and p-anisaldehyde to give characteristic colours for their detection. Because of this, together with the complexity of the mixtures that are now known to occur naturally, the analytical method of choice for quantitative results today is often GC either with electron capture or mass spectrometric detection (MS). Recently, LC-MS, has been employed for the determination and identification of trichothecenes at trace levels. In addition, reliable and quite sensitive HPLC methods have been developed for some of the Group B compounds.

Immunoassays are available as screening tests for DON, T-2- and HT-2 in cereals or for rapid screening of trichothecenes. Accurate quantification by immunological assays is often prevented or limited due to cross reactivity. Future development of more specific antibodies may improve quantification and sensitivity.

Stability and Persistence

The trichothecene structure is quite stable so that most compounds are relatively unchanged during processing although the number of studies reported is limited. Recent studies have shown that when flour containing deoxynivalenol was used to produce bread using fermentation temperatures between 30° and 50° C. the maximum reduction in concentration was about 50%. The effects of moisture, pH and heat on the stability of nivalenol and deoxynivalenol in naturally contaminated ground maize were shown to be relatively small over a pH range of 1-10. Conditions of pH 12, high salt concentration and 80° C. for a prolonged time were required to give substantial breakdown.

[The above section is adapted from the European Mycotoxin Awareness Network (EMAN) web site at http://www.mycotoxins.com]

Deoxynivalenol (DON)

The trichothecene mycotoxin may comprise deoxynivalenol.

Deoxynivalenol is also known as DON, vomitoxin, dehydronivalenol or 12,13-epoxy-3,7,15-trichothec-9-en-8-one. It has the molecular formula $C_{15}H_{20}O_6$. The IUPAC name is (3α,7α)-3,7,15-trihydroxy-12,13-epoxytrichothec-9-en-8-one.

Deoxynivalenol has CAS number 51481-10-8, PubChem number 40024, ChemSpider number 36584, KEGG number C09747 and ChEMBL number CHEMBL513300.

Deoxynivalenol is one of about 150 related compounds known as the trichothecenes that are formed by a number of species of *Fusarium* and some other fungi. Because deoxynivalenol is toxic and often found in foodstuffs, sometimes in high concentrations, it has recently been of concern to International Organisations and Government Food Agencies.

Deoxynivalenol is nearly always formed before harvest when crops are invaded by certain species of *Fusarium* such as *F. graminearum* and *F. culmorum*. These two species are important plant pathogens and cause *Fusarium* heat blight in wheat and *Gibberella* ear rot in maize. Deoxynivalenol is thermally stable so once formed it is likely to persist through storage and the food chain.

Chemical and Physical Properties

Figure 3:
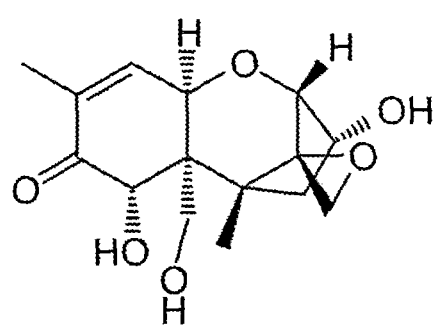
FIG. 3 shows the chemical structure of deoxynivalenol (DON).

Deoxynivalenol is a member of the 12,13-epoxy-trichothecenes class of sesquiterpene mycotoxins. Its chemical structure is shown in FIG. 3.

It is produced primarily by the fungus *Gibberella zeae* (Schwein.) *Petch* (anamorph=*Fusarium graminearum* Schwabe), which infects corn, small grains and mixed feeds (Hart et al., J. Agric. Food Chem. 31: 657-659 (183); Hart et al., Plant Dis. 66: 1133-1135 (1982); Neish et al., Can. J. Plant Sci. 61: 811-815 (1981)).

At the cellular level, the primary toxic effect of DON is inhibition of protein synthesis by binding to the 60S ribosomal subunit, which interferes with peptidyltransferase (Betina, Chem. Biol. Interact. 71: 105-146 (1989); Weber et al., Biochem. 31: 9350-9354 (1992)). DON can cause anorexia and emesis in animals (Scott et al. Proc. natl. Acad. Sci. USA 89: 5398-5402 (1992)). Other toxic effects of DON include skin irritation, hemorrhaging, hematological changes, human lymphocyte blastogenesis impairment, radiomimetic effects, apoptosis and immunotoxicity (Scott et al. ibid.).

DON is primarily found as a contaminant in grains that are infected with the above fungi. It has also been implicated as a chemical warfare agent. Currently, the only means for eliminating DON from human and animal foodstuffs is to detect DON in food and to remove any contaminated foodstuffs from the food supply.

Deoxynivalenol is one of the more polar trichothecenes with a molecular weight of 296.32. It contains one primary and two secondary hydroxyl groups and is soluble in water and polar solvents such as methanol and acetonitrile.

Unlike many of the other trichothecenes the deoxynivalenol molecule contains a conjugated carbonyl system and this results in some UV absorbance that assists its detection by TLC or HPLC methods. In contaminated cereals 3- and 15-acetyl deoxynivalenol can co-occur in significant amounts with deoxynivalenol. It is chemically very stable.

Toxicity and Importance

Acute toxicity of deoxynivalenol is characterised by vomiting particularly in pigs, feed refusal, weight loss and diarrhoea. Acute intoxication may produce necrosis in various tissues such as the gastrointestinal tract, bone marrow and lymphoid tissues.

Subchronic oral exposure in experimental animals, pigs, mice and rats may also lead to reduced feed intake and slowed weight gain and changes in some blood parameters including serum immunoglobulins. Studies suggest that deoxynivalenol may have effects on the immune system. There are no indications of carcinogenic, mutagenic or teratogenic effects.

A study reporting human food poisoning by infected wheat containing deoxynivalenol in India showed a range of symptoms including abdominal pains, dizziness, headache, throat irritation, nausea, vomiting, diarrhoea and blood in the stool.

Products Affected and Natural Occurrence

The main commodities affected are cereals. Deoxynivalenol is a frequent contaminant of grains such as wheat, buckwheat, barley, oats, triticale, rye, maize, sorghum and rice.

Using methods with sensitivities of about 5 μg/kg it is possibly to show that more than 50% of samples may be contaminated when the appropriate species of *Fusarium* infect growing cereals. Concentrations have been reported up to as high as 9 mg/kg in barley and 6 mg/kg in wheat. Because it is a stable compound it has also been detected in a range of processed cereal products including breakfast cereals, bread, noodles, infant foods, malt and beer. The presence of deoxynivalenol in barley causes the problem of gushing in beer.

However, the transfer of deoxynivalenol from animal feed to meat and other animal products appears to be extremely small. The formation of deoxynivalenol in growing crops is dependent on climate and will thus vary between geographical region and year.

Sampling and Analysis

Representative sampling is important as it is with other mycotoxins in cereals. Its distribution in bulk grain has been poorly studied and sampling plans derived for other mycotoxins such as aflatoxin and ochratoxin A should be followed.

Deoxynivalenol can be extracted from cereals using aqueous solvent mixtures such as methanol and water or acetonitrile and water. Because deoxynivalenol has some UV absorbence it is possible to detect it using TLC or HPLC although the sensitivity of these techniques is relatively poor. ELISA based methods have been developed and commercial kits are available. Such methods should be thoroughly evaluated before use. However, the most sensitive method is GC usually in tandem with a mass spectrometer. The advantage of this is that other related compounds can be determined simultaneously and high sensitivity attained. The disadvantages are that deoxynivalenol is non-volatile must be derivatised to form a stable derivative suitable for analysis and that expensive equipment and skilled operators are required for its operation.

Stability and Persistence

Deoxynivalenol is thermally stable so it is difficult to eliminate from grain once formed. During the milling process of wheat it fractionates so that the higher levels concentrate in the outer bran layers and the concentration in white flour is lower than in the original grain. Because deoxynivalenol is water soluble a significant proportion can be removed by washing grain but commercially this represents an additional stage and an effluent problem. Enzymic reactions have been shown both to reduce and increase levels of deoxynivalenol. This is most likely due to the inter-conversion of related molecules or precursors.

[The above section is adapted from the European Mycotoxin Awareness Network (EMAN) website at http://www.mycotoxins.com]

Composition

The composition described here comprising non-digestible oligosaccharide(s) may comprise an enteral composition, i.e., anything that is enterally administered, such as orally. In particular, the enteral composition may comprise a foodstuff, such as nutritional composition or nutritional food.

As used in this document, the term "enteral" is intended to refer to the delivery directly into the gastrointestinal tract of a subject (e.g. orally or via a tube, catheter or stoma).

The composition may comprise an infant and/or toddler nutrition, such as an infant and/or toddler formula. The composition may comprise a children's nutritional product. It may comprise a pediatric nutritional product or formula, a toddler nutritional formula, growing up milk, human milk supplement or medicinal food.

The composition may in one embodiment be used as an infant formula. The composition may be applied as a complete nutrition for infants. Such food may comprise lipid, protein and carbohydrate and may be administered in liquid form.

In a further embodiment, the composition may comprise a ready-to-use liquid food, e.g. is in a ready-to-feed liquid form. A packed ready-to-use liquid food may involve fewer steps for preparation than a powder to be reconstituted and hence may involve a reduced chance of contamination by harmful micro-organisms.

The composition described here may comprise an infant and/or toddler nutrition which for example comprises between 5 and 50 en % lipid, between 5 and 50 en % protein, between 15 and 90 en % carbohydrate and non-digestible oligosaccharide A and/or B. In some embodiments, the composition may comprise an infant and/or toddler nutrition comprising between 35 and 50 en % lipid, between 7.5 and 12.5 en % protein and between 35 and 80 en % carbohydrate (en % is short for energy percentage and represents the relative amount each constituent contributes to the total caloric value of the preparation).

The composition comprising non-digestible oligosaccharides may comprise lipids, such as vegetable lipids, and/or at least one oil selected from the group consisting of fish, animal, algae and bacterial oil. The composition may comprise long chain polyunsaturated fatty acids (LC-PUFA), such as eicosapentaenoic acid (EPA) and/or docosahexaenoic acid (DHA), and/or docospentanenoic acid (DPA), and/or arachidonic acid (ARA).

The composition comprising non-digestible oligosaccharides may comprise proteins. The proteins used in the nutritional preparation may be selected from the group consisting of non-human animal proteins (such as milk proteins, including caseins and whey proteins, meat proteins and egg proteins), vegetable proteins (such as soy protein, wheat protein, rice protein, potato protein and pea protein), hydrolysates (partially and/or extensively), free amino acids and mixtures thereof. The protein of the infant nutrition may be selected from the group consisting of hydrolysed milk protein (e.g. hydrolysed casein and/or hydrolysed whey protein), hydrolysed vegetable protein and/or amino acids. The use of these proteins may reduce the allergic reactions of the infant and/or toddler and/or increase protein absorption.

The protein source may be extensively and/or partially hydrolysed. The protein source may be extensively hydrolysed whey protein derived from cow's milk.

The composition comprising non-digestible oligosaccharides may comprise digestible carbohydrates. The digestible carbohydrates used in the nutritional preparation may be selected from the group consisting of sucrose, lactose, maltose, galactose, glucose, fructose, corn syrup solids, starch and maltodextrins, and mixtures thereof, such as lactose.

The composition comprising non-digestible oligosaccharides may comprise minerals, trace elements and vitamins, choline, taurine, carnitine, myo-inositol and/or mixtures thereof. The composition comprising non-digestible oligosaccharides may comprise nucleotides. The composition may comprise cytidine 5'-monophospate, uridine 5'-monophospate, adenosine 5'-monophospate, guanosine 5'-monophospate, and inosine 5'-monophospate.

The composition comprising non-digestible oligosaccharides may comprise a non-fermented composition. Fermentation by micro-organisms results in a lowering of the pH. The composition may have a pH above 5.5, such as 6.0, such as 6.5 in order to reduce damage to teeth. The pH may be between 6 and 8.

The composition may be formulated so that it does not have an excessive caloric density, however still provides sufficient calories to feed the subject. Hence, the liquid food may have a caloric density between 0.1 and 2.5 kcal/ml, such as a caloric density of between 0.4 and 1.2 kcal/ml, such as between 0.55 and 0.75 kcal/ml.

The composition comprising non-digestible oligosaccharides may have a viscosity between 1 and 60 mPa·s, such as between 1 and 20 mPa·s, such as between 1 and 10 mPa·s, such as between 1 and 6 mPa·s. The low viscosity ensures a proper administration of the liquid, e.g. a proper passage through the hole of a nipple. Also this viscosity closely resembles the viscosity of human milk. Furthermore, a low viscosity results in a normal gastric emptying and a better energy intake, which is essential for infants and/or toddlers which need the energy for optimal growth and development. The composition may be prepared by admixing a powdered composition with water. Normally infant formula is prepared in such way.

The composition described here may be made up as a packaged power composition wherein said package is provided with instruction to admix the powder with a suitable amount of liquid, thereby resulting in a liquid composition with a viscosity between 1 and 60 mPa·s.

The viscosity of the liquid may be determined using a Physica Rheometer MCR 300 (Physica Messtechnik GmbH, Ostfilden, Germany) at shear rate of 95 $s^{-1}$ at 20° C.

The composition comprising non-digestible oligosaccharides may have a long shelf life. For example, it may be shelf stable at ambient temperature for at least 6 months, such as at least 12 months, where it is in a liquid, ready-to-feed form.

Growing Up Milk and Cereal

The composition comprising non-digestible oligosaccharides may in particular comprise a cereal or a growing up milk. Cereals are described in more detail below.

The non-digestible oligosaccharide composition may therefore comprise a children's nutritional composition provided as a growing-up milk or cereal.

In an embodiment, sources of carbohydrate for use in the growing-up milk or cereal may include maltodextrin, fructose, lactose, prebiotics, resistant starch, starch, and any combinations thereof.

Where the composition comprises a growing-up milk or cereal formulated for children between the ages of 1 to 6 years, vitamins and minerals may be added in varying amounts and ranges based on a per-serving basis. In an embodiment, one serving of the growing-up milk or cereal may contain from about 15% to about 50% of the Estimated Average Requirement (EAR) for children between the ages of 1 and 6 years for the following nutrients: vitamin E, vitamin K, niacin, pantothenic acid, vitamin B12, biotin, choline, potassium, magnesium, phosphorus, chloride, copper, selenium, fluoride, and any combinations thereof. In an embodiment, one serving of the growing-up milk or cereal may contain from about 20% to about 30% of the EAR for children between the ages of 1 and 6 years for the following nutrients: vitamin E, vitamin K, niacin, pantothenic acid, vitamin B12, biotin, choline, potassium, magnesium, phosphorus, chloride, copper, selenium, fluoride, and any combinations thereof. Any known sources of these nutrients having nutritional uses may be suitable for use in the composition.

The composition such as growing up milk or cereal may optionally contain other substances that may have a beneficial effect on the host such as lactoferrin, nucleotides, nucleosides, immunoglobulins, CMP equivalents (cytidine 5'-monophosphate, free acid), UMP equivalents (uridine 5'-monophosphate, disodium salt), AMP equivalents (adenosine 5'-monophosphate, free acid), GMP equivalents (guanosine 5'-monophosphate, disodium salt) and combinations thereof.

Cereals

As noted above, the composition comprising non-digestible oligosaccharides may comprise a cereal.

Accordingly, the non-digestible oligosaccharide composition described here may comprise a cereal component. Cereal components are an important part of the infant's diet, and are usually one of the first non-breast milk and non-infant formulae components introduced into the diet of infants. Ultimately, the infant will consume a high cereal diet, including bread, rice and pasta.

The cereal component may comprise a component selected from the group consisting of whole cereal, cereal flour, milled cereal, ground cereals, cereal starch, and cereal fibre. The cereal component may for example comprise a component selected from the group consisting of cereal flour, ground cereal and milled cereal. The cereal flour may in some embodiments comprise cereal flour which is dextrinised by heat treatment and/or cereal flour which has been enzyme treated in order to degrade the cereal starch.

The non-digestible oligosaccharide composition described here may comprise a precooked cereal component, such as precooked cereal flour. The term "precooked cereal flour" indicates flour obtained by the process whereby flour, in granular and crystalline structure is swelled and transformed, for example in a continuous amorphous phase, in the presence of heat and water, dried (e.g. using drum drying or extrusion cooking) and ground.

The precooked flour may comprise between 5 and 15 wt. % protein based on the total dry weight of the precooked flour. The use of precooked flour may be such that the final product has a reduced content of thermo-resistant spores compared to the use of non-precooked flour. Furthermore, the use of precooked may be such that the viscosity of the composition is more stable after reconstitution of the product with a warm liquid. This is in contrast to the situation wherein solely non-precooked flour is used. In the latter case the viscosity gradually increases with time.

The precooked flour if present may have a degree of gelatinisation of at least 50%, such as at least 75%. This gives better water holding capacity (WHC), resulting in an improved product (e.g. stability and palatability). The WHC of the precooked material may be between 2 and 10 g water/g dry matter precooked material, such as between 2.5 and 5 g water/g dry matter precooked material. The WHC can be determined as described by Pinnavaia and Pizzirani (Starch/Stärke 50 (1998) nr. 2-3, S. 64-67).

The non-digestible oligosaccharide composition described here may comprise at least one cereal selected from the group consisting of rice, millet, sorghum, wheat, barley, buckwheat, maize (corn), fonio, oats, rye, triticale, teff, wild rice, spelt, amaranth, quinoa and starchy root crops. Starchy root crops may be selected from the group consisting of potato, sweet potato, cassava, yams, aroids, oca, ulluco and mashua.

The composition may be gluten free. The intake of gluten by infants below 6 month of age may result in gastrointestinal damage. In some embodiments, therefore, the composition may comprise one or more cereal components selected from the group consisting of rice, maize and millet, sorghum, teff, oat and starchy root crops. For example, the composition may comprise one or more cereal components selected from the group consisting of rice, maize and millet, teff, and oat. The composition may consist of rice, maize and millet, sorghum, teff, oat, starchy root crops and mixtures thereof. The cereal may be selected from the group consisting of rice, maize, oat, teff and millet. The cereal part of the composition may comprise mixture of cereal components. Typically the cereal is processed as defined in EU directive 96/5/EC.

The composition described here may comprise between 10 and 99 g cereal component per 100 g dry weight of the composition, such as between 20 and 90 g, such as between 25 and 80 g.

Viscosity

The composition comprising non-digestible oligosaccharides may have a viscosity of between 150 and 100,000 mPas at 20° C. and at a shear rate of 10 s-1, such as between 250 and 25,000 mPas, such as between 300 and 10,000 mPas, such as between 500 and 10,000 mPas such as between 1000 and 10,000 mPas. The composition may have a semi-liquid and/or semi-solid constitution. Solid food is still inappropriate for infants changing from breast milk or infant liquid, because of the infant's lack of teeth and its poor swallowing reflex. Semiliquid may refer to food products that have a viscosity above 150 mPas, but are still pourable. Semi-solid may refer to products that are still formable or spreadable but not pourable, with a viscosity up to 100,000 mPas.

Unless specified otherwise, whenever the term viscosity is used in this document, this refers to the physical parameter which is determined according to the following method: Shear flow viscosities were determined in a Paar Physika MCR 300 Modular Compact Rheometer. The instrument was equipped with a concentric cylinder geometry with a diameter of 27 mm. A logarithmic shear rate ramp is used from 0.1 to 1000 $s^{-1}$ in 20 minutes having 40 measurement points. Using the same geometry viscosities can also be measured in shear flow at a constant shear rate of 10 $s^{-1}$ for 10 minutes. The rheometer's thermostat is set on the appropriate temperature (i.e. 20° C.).

To prevent intestinal discomfort, the osmolarity of the semi-liquid and/or semi-solid may be between 300 and 600 mOsm/l, such as between 400 and 500 mOsm/l.

The composition comprising non-digestible oligosaccharides may be in a ready-to-eat form, in which the liquid is already present. In such a form, the product needs only to be heated before consumption and has a stable viscosity during consumption.

The composition comprising non-digestible oligosaccharides may be in the form of granules, flakes, puffs and/or shreds, such as granules.

Powder

The non-digestible oligosaccharide composition may be in the form of a powder composition.

This may comprise: 10 to 99 wt. % cereal based on dry weight of the powder composition; 1.0 to 30 wt. % fibre based on dry weight of the powder composition; and one or more non-digestible oligosaccharides as described in this document.

Reconstitution of this powder with a liquid (such as water or milk) may yield a composition with a viscosity of between 150 and 100,000 mPas. For example, 10 to 100 g powder may be reconstituted with 140 ml liquid (such as water), such as 14 to 80 g powder, such as 30 to 65 g powder, such as 40 to 60 g is reconstituted with 140 ml liquid. For example, the liquid may have a temperature of 30-70° C. upon mixing with the powder.

We describe a packaging containing powder composition, wherein the packaging indicates that the powder composition is to be mixed with a suitable amount of liquid.

The powder may be in an agglomerated and/or granulated form with an average particle size below 2 mm, such as below 1 mm. For example, the composition may comprise milk protein, calcium, lactose and fat. This has the advantage that the dried product can be reconstituted with water instead of milk. Water advantageously is more readily available and less prone to contamination than milk. For example, the fat is of vegetable origin. This has the advantage that a healthier product is obtained than when the dried product is reconstituted with cow's milk comprising more saturated fat.

Administration

The composition described here may be administered to a number of subjects.

For example, it may be administered to prematurely born babies, maturely born babies, infants which are in the adaptation period to solid food, infants and/or toddlers such as with an increased risk for or suffering from allergy, and/or infants and/or toddlers such as with an increased risk for infections, such as infants and/or toddlers attending day care centres, or suffering from infections. The subject may also be a child, teenager or adult.

We therefore provide a method for providing nutrition to a human infant and/or toddler, comprising administering to the infant and/or toddler the composition described here. The infant and/or toddler may have an age between 0 and 36 month, such as between 0 and 18 month, such as between 0 and 12 months. We therefore provide a method for providing nutrition to a human infant with the age of 0-12 months. We further provide a method for providing nutrition to a human toddler with the age of 12-36 months.

We also provide for a method for stimulating the health of an infant and/or toddler, comprising administering a composition comprising a non-digestible oligosaccharide A and/or B to the infant and/or toddler.

We further provide for a method for stimulating the health in an infant and/or toddler comprising the steps a) admixing i) a nutritionally or pharmaceutically acceptable liquid; and ii) a dry composition, wherein the dry composition comprises a non-digestible oligosaccharide A and/or B, and step b) administering the composition obtained in step a) to an infant and/or toddler.

EXAMPLES

Example 1

Introduction

Mycotoxins are toxic natural secondary metabolites formed by fungi growing on agricultural commodities in the field or during storage. At global level, it is considered that 25% of the world crop production is contaminated by mycotoxins, which may be a risk factor for human health due to their toxic properties and their high stability to heat treatment. One of the most prevalent trichothecene mycotoxins is deoxynivalenol (DON). In humans, food contamination with DON causes gastro-intestinal illness with specific lesions observed at the intestinal levels as well as the increased susceptibility to intestinal infections and DON can promote inflammatory processes in the gut. Oligosaccharides positively affect the composition of the microflora and/or the activity in the gastrointestinal tract and these compounds have been associated with immune-modulating effects in the intestine. The oligosaccharide fraction is a major component of human breast milk. The aim of this example is to investigate the effect of DON on epithelial integrity and whether oligosaccharides affect the DON related pathological effects to the intestinal epithelial layer. In this example the ability of galacto-oligosaccharides (GOS) to inhibit the DON-related effects was investigated.
Materials and Methods The human epithelial colorectal adenocarcinoma Caco-2 cell line was obtained from American Type Tissue Collection (passages 5-19) and were cultured in 75 cm2 culture flasks in Dulbecco's modified Eagle's minimum essential medium (DMEM), containing 25 mM Hepes, 4.5 g/l glucose supplemented with 10% heat-inactivated FCS, Penicillin (100 U/ml)/Streptomycin (100 µg/ml), Glutamine (2 mM) and Non-essential Amino Acids (1%). The cell cultures were maintained in a humidified atmosphere of 95% air and 5% $CO_2$ at 37° C. Medium was refreshed every 2-3 days and cells were passaged once a week. For subculture, the confluent cells were dispersed by treatment with 0.05% trypsin and 0.54 M ethylene diamine tetraacetic acid (EDTA) and were diluted in the complete culture medium.

Using the Caco2 cells in a transwell system as an in vitro model, we studied the effect of DON on transepithelial electrical resistance (TEER), luciferase yellow (LY) permeability, tight junction protein expression, cytokine release, intracellular inflammatory cascades (NF-κB), galectin expression and release (contain carbohydrate recognition domains) and cell viability.

Purified DON was diluted in absolute ethanol (99.9%) to prepare a 25 mM stock solution and was stored at −20° C. Serial dilutions of mycotoxins were prepared in DMEM medium.

Figure 4:
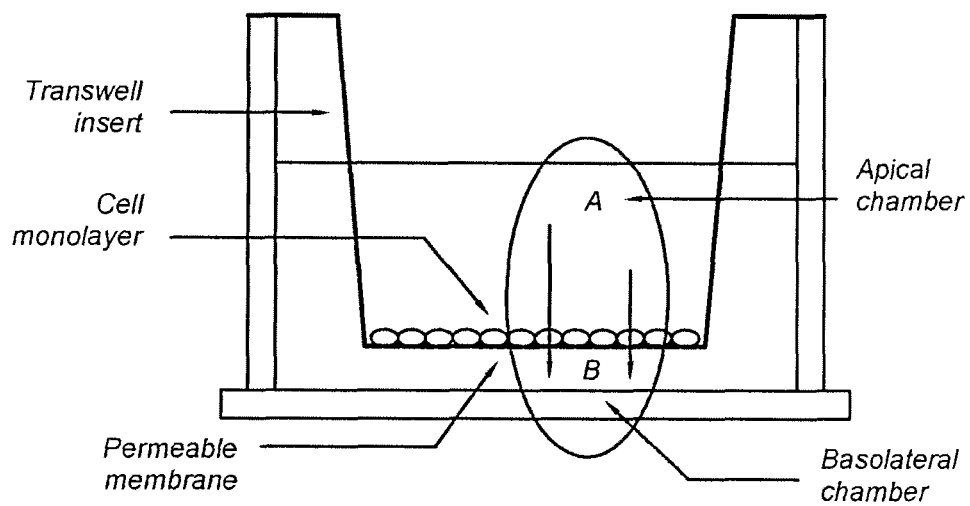
FIG. 4 shows an in vitro transwell system that is used to mimic the human small intestine.

The transwell system is shown as FIG. 4.

Results—Transepithelial Electrical Resistance (TEER) Assay

Figure 5:
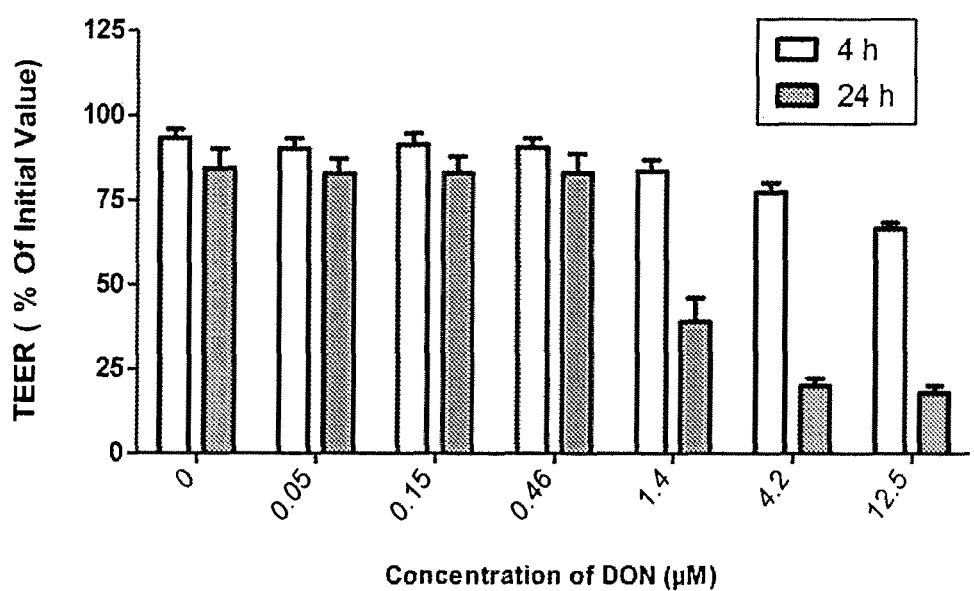
FIG. 5 shows the reduction of the trans-epithelial electrical resistance (TEER) with increasing concentrations of DON, indicating that the confluence of the cellular monolayer is disrupted.

The results of the transepithelial electrical resistance (TEER) assay are shown in FIG. 5. The TEER of Caco-2 cells was dose-dependently reduced after DON incubation, indicating that the confluence of the cellular monolayer is disrupted.

Results—Luciferase Yellow (LY) Permeability Assay

Caco-2 cells were grown on inserts as described above and treated for 24 h with either vehicle or DON. Two different membrane-impermeable molecules, Lucifer yellow (molecular mass of 457 Da) and fluorescein isothiocyanate-dextran (FITC-dextran; data not shown) (molecular mass of 4 and 40 kDa) were served as paracellular markers for determining the integrity of the cell monolayer. The transport studies from apical side to basalateral side with 6 µg/ml of lucifer yellow or FITC-dextran at the apical chamber were performed. To evaluate the permeability of the monolayers, apical and basolateral compartment media were collected after 4 h incubation at 37° C. in a humidified atmosphere of 95% air and 5% $CO_2$. The amount of these tracers were determined by measuring the fluorescence intensity using a spectrophotofluorimeter at excitation and emission wavelengths of 410 and 520 nm for Lucifer yellow or 485 and 520 nm for FITC-dextran.

Figure 6:
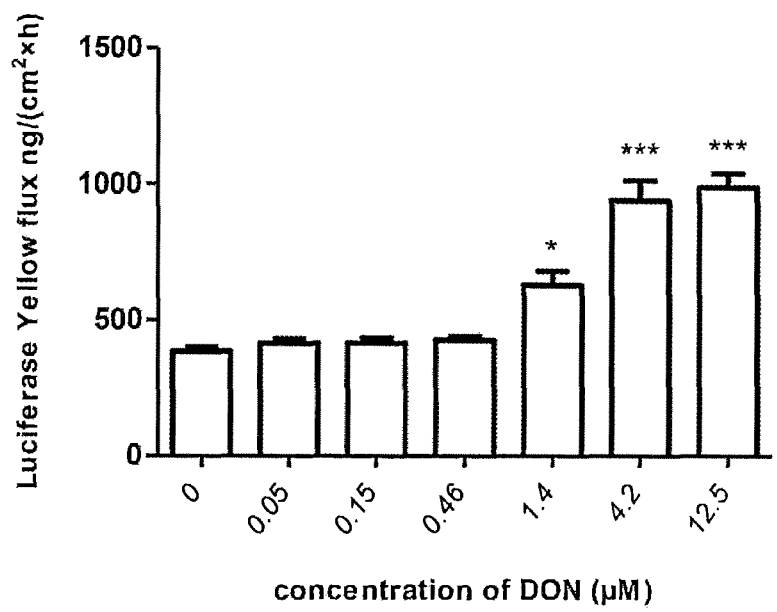
FIG. 6 shows the induced transport of luciferase yellow (LY) to the basolateral chamber due to increasing concentrations of DON, indicating increased permeability of the cellular monolayer.

The results of the luciferase yellow (LY) permeability are shown in FIG. 6. A significant increase in the transport of luciferase yellow (LY) towards the basolateral chamber due to increasing concentrations DON indicates an increased permeability of the cellular monolayer.

Results—Cell Viability Assay

Caco-2 cells were grown on inserts as described above and treated for 24 h with either vehicle or DON. Lactate Dehydrogenase (LDH) was detected in the culture supernatant using specific detection kits in accordance with the manufacturer's instructions.

Figure 7:
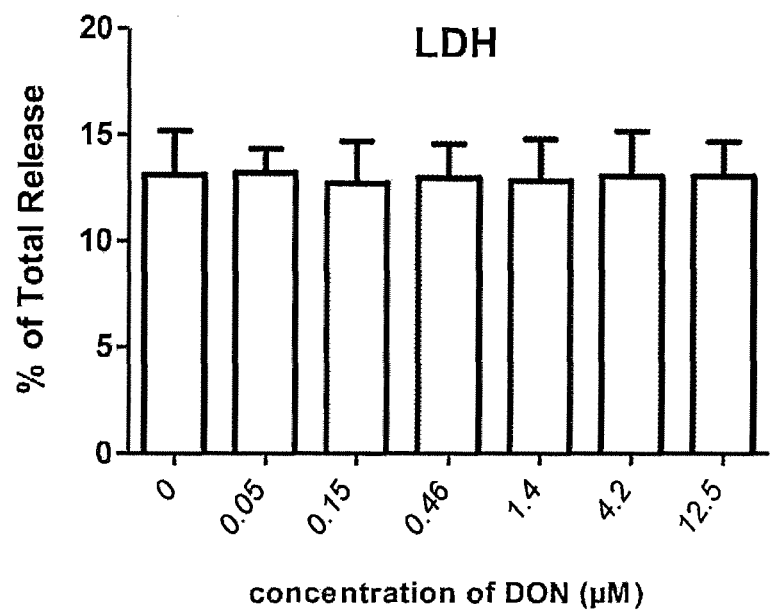
FIG. 7 shows a representative example of the unaltered cell viability with increasing concentrations of DON. Although the depicted cell viability is determined with the LDH assay, other viability assays such as the MTS and MTT also show similar results.

The result of the LDH cell viability assay is shown in FIG. 7. This figure is a representative example of the unaltered cell viability with increasing concentrations of DON. Although the depicted cell viability is determined with the LDH assay, other viability assays (MTS and MTT assay) also show similar results.

Results—IL-8 Assay

Caco-2 cells grown on inserts were incubated in the presence or absence of DON and the production of cytokines in the collected supernatants was measured by means of ELISA. For IL-8 determination, high binding EIA/RIA 96 well plates were coated with anti-human IL-8 monoclonal antibody dissolved in 0.1 M sodium carbonate in phosphate buffer saline (PBS) and incubated overnight at 4° C. Plates were washed with 0.05% Tween-20 in 10% PBS/milli-Q water and blocked with 0.5% bovine serum albumin (BSA) in PBS for 1 h at RT. Subsequently, blocking buffer was discarded and 50 µl of sample or diluted IL-8 standard was added to the wells and incubated for 2 h at RT. Plates were washed with 0.05% Tween-20 in 10% PBS/milli-Q water followed by incubation in the dark with biotinylated anti-human IL-8 monoclonal antibody mixed with Streptavidine-horseradish peroxidase (HRP) dissolved in 0.1% Tween-20 in 0.5% BSA/PBS for 1 h at RT. After washing, TetraMethylBenzidine, used as a visualizing reagent, was added to the plate and incubated in the dark for 20 min at RT. The reaction was stopped with 1M $H_2SO_4$, and optical density was measured at 450 nm using a microplate reader. IL-6 and TNF-α determination was also performed according to the manufacturer's protocol.

Figure 8:
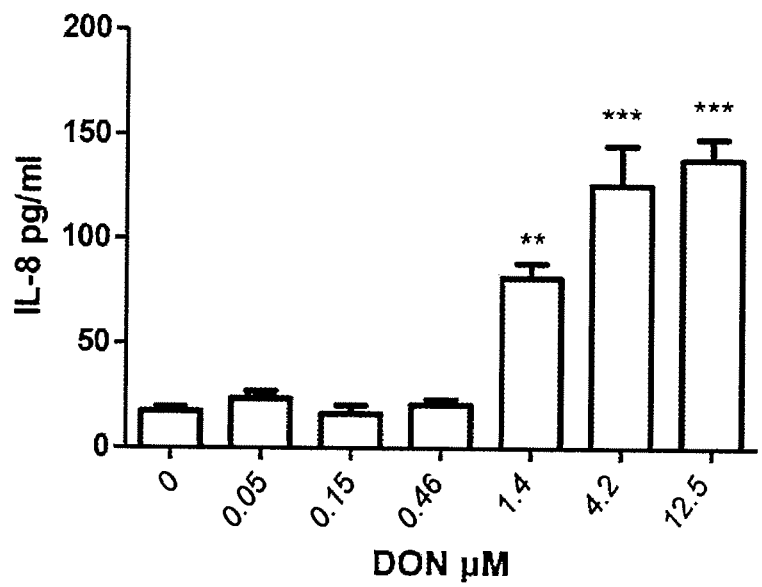
FIG. 8 shows the production of the pro-inflammatory cytokine IL-8 by the cellular monolayer into the basolateral chamber after increasing dosages of DON. Similar IL-8 levels are observed in the apical chamber.

The dose-dependent production of the pro-inflammatory cytokine IL-8 by the cellular monolayer into the basolateral chamber after increasing dosages of DON is shown in FIG. 8.

Similar IL-8 levels are observed in the apical chamber. In contrast, the levels of IL-6 and TNF-α are below the detection limit.

Results—Localisation of Tight Junction Proteins

Caco-2 cells grown on inserts were used for Immuno-HistoChemistry staining of different tight junction proteins.

Figure 9:
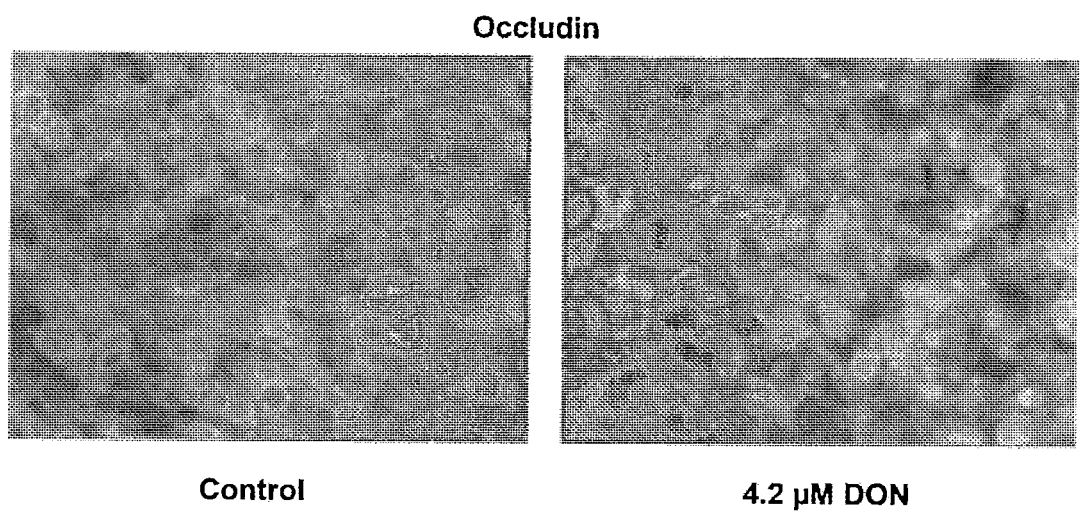
FIG. 9 shows a representative example of the tight junction proteins that are translocated by DON exposure from the cell membrane towards the inner cell. Immunofluorescence microscopy was used to identify the translocation of occludin, claudin-1, claudin-4 and ZO-1 in non-stimulated cells as well as the DON- (4.2 μM) stimulated cells.

A representative example of the translocation of tight junction protein Occludin from the cell membrane towards the inner cell is shown in FIG. 9.

Besides the translocation of Occludin, immunofluorescence microscopy was used to identify the translocation of claudin-1, claudin-4 and ZO-1 in non-stimulated cells as well as the DON- (4.2 mM) stimulated cells.

Results—GOS Reverses the Effects of DON

Figure 10:
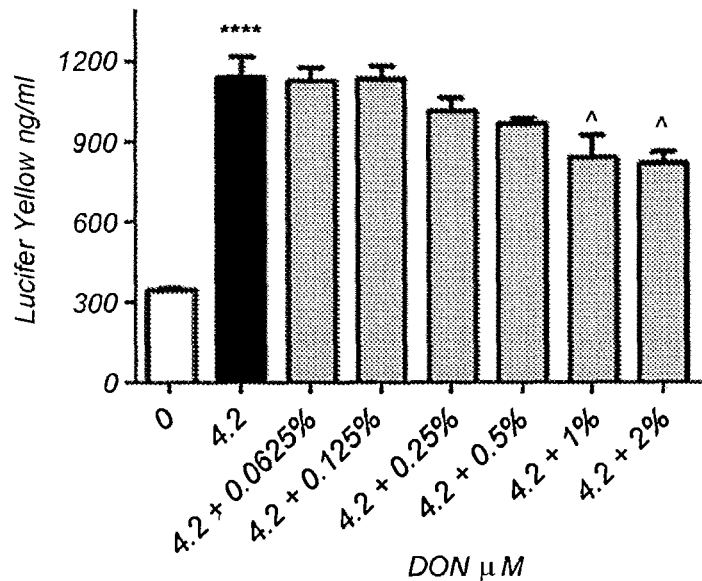
FIG. 10 shows that the DON-induced LY transport is decreased by 1-2% GOS.

The results of the luciferase yellow test with DON and GOS are shown in FIG. 10. The transport of LY after DON-induced damage is decreased by 1-2% GOS. GOS used in these studies were commercially available and had a DP 2-6.

Figure 11:
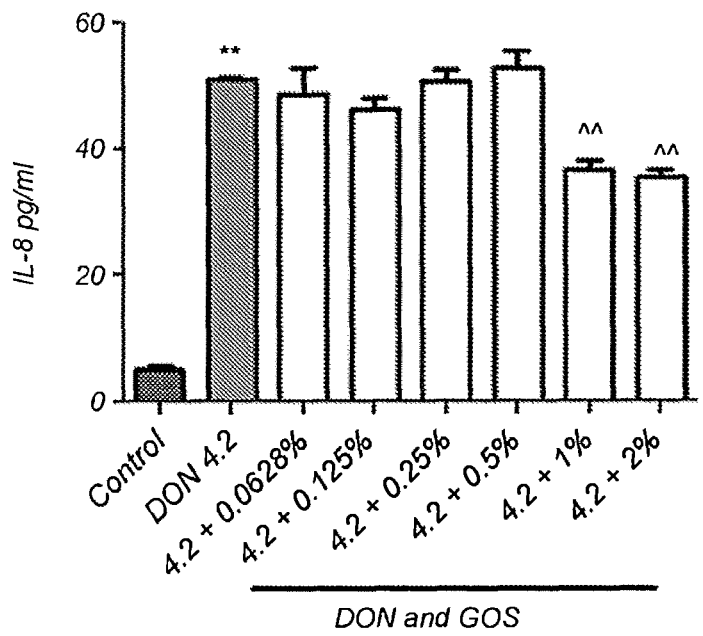
FIG. 11 shows that the DON-induced IL-8 production is decreased by 1-2% GOS in the basolateral chamber. Similar findings were observed in the apical chamber.

FIG. 11 shows that the DON-induced IL-8 production is decreased by 1-2% GOS in the basolateral chamber. Similar findings were observed in the apical chamber.

Conclusion

The mytoxin DON impaired intestinal barrier function and induced an inflammatory response of epithelial cells. We conclude that GOS can restore the DON-induced effect on epithelial barrier function and exert an anti-inflammatory effect by reducing IL-8 levels. The results suggested that the intake of galacto-oligosaccharides can reduce the direct effects of DON on the intestinal epithelial integrity. Taken together, the use of oligosaccharides to restrict the pathological effects of DON related to intestinal epithelial cells offers considerable promise for mycotoxin exposure intervention.

Example 2

The aim of this example is to investigate whether oligosaccharides affect the DON related pathological effects to the intestinal epithelial layer. In this example the ability of fructooligosaccharides and galactooligosaccharides to inhibit the DON-related effects was investigated.

Materials and Methods

Reference is made to the corresponding section in example 1. The fructooligosaccharides investigated had a degree of polymerisation of 2-8, and was available from Beneo-Orafti (Wijchen, The Netherlands). TEER and LY assessment were carried out as detailed in example 1.

Results—GOS and FOS Reverse the Effects of DON

Figure 12A:
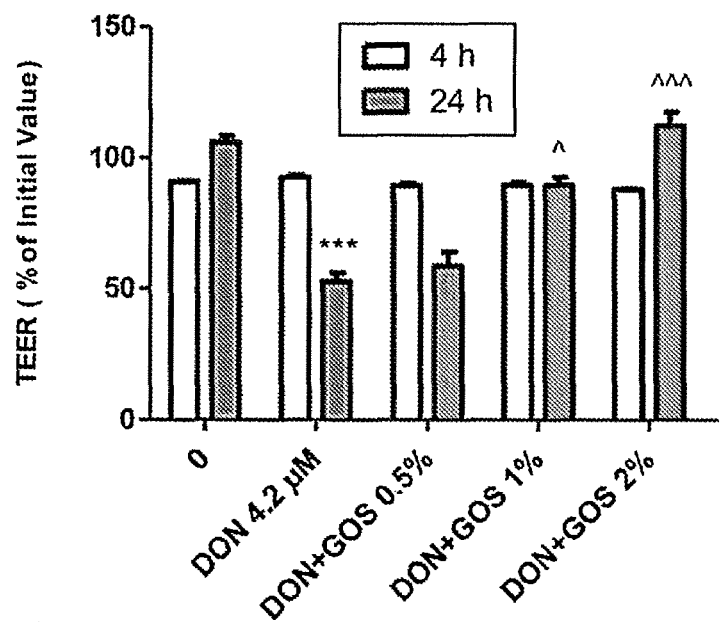
FIGS. 12A and 12B show the ameliorating effect of GOS (DP 2-6) and FOS (DP 2-8) on the decreased reduction of the trans-epithelial electrical resistance (TEER) induced by DON- (4.2 μM) stimulated cells. There was no effect observed on TEER for non-stimulated cells (not shown).
Figure 12B:
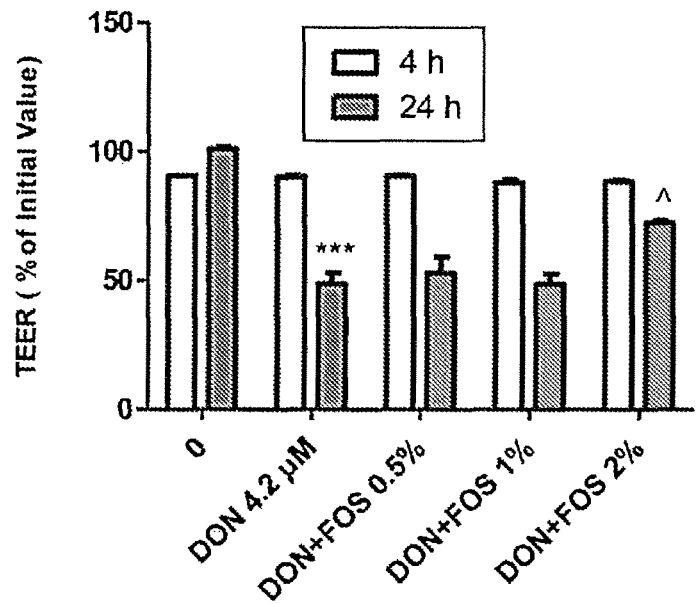

Following the results of the DON-induced reduction in transepithelial electrical resistance (TEER) assay shown in FIG. 5, the TEER of Caco-2 cells was investigated for various concentrations of GOS and FOS. Ameliorating effects are found in both cases. The results are plotted in FIGS. 12A and 12B, respectively. The results observed for GOS confirmed the findings reported in example 1.

Figure 13:
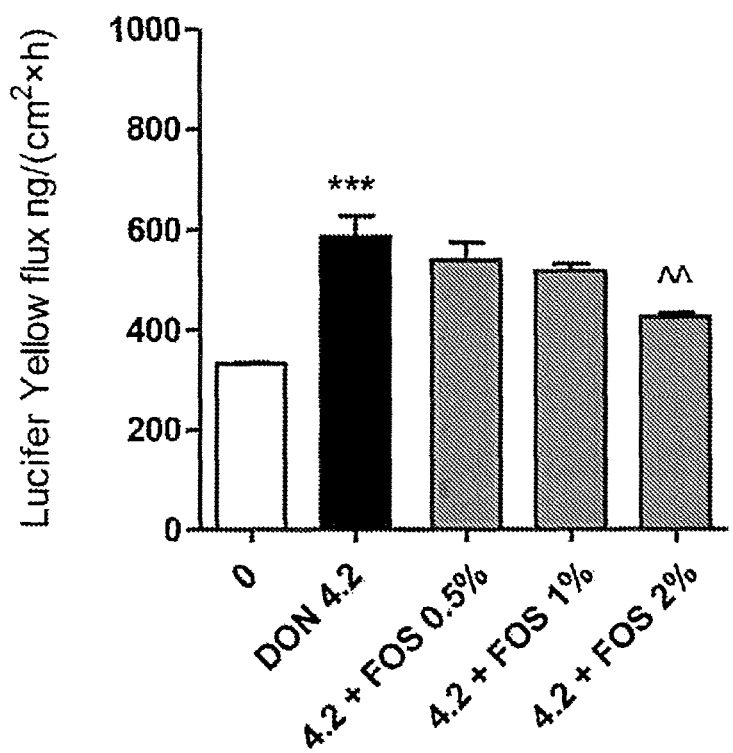
FIG. 13 shows that the DON-induced LY transport is decreased by FOS.

The results of the luciferase yellow test with DON and FOS are shown in FIG. 13. The transport of LY after DON-induced damage is decreased by FOS.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method for the treatment or alleviation of a trichothecene mycotoxin exposure associated condition in a human baby, infant, toddler, or young child suffering from same, comprising administering to the human baby, infant, toddler, or young child a composition comprising a non-digestible oligosaccharide having a degree of polymerisation (DP) of 2-10.

2. The method according to claim 1, wherein the trichothecene mycotoxin comprises deoxynivalenol.

3. The method according to claim 1, wherein the non-digestible oligosaccharide comprises a galactooligosaccharide and/or a fructooligosaccharide.

4. The method according to claim 3, wherein the non-digestible oligosaccharide comprises a transgalacto-oligosaccharide.

5. The method according to claim 3, wherein the non-digestible oligosaccharide composition comprises a galacto-oligosaccharide (GOS).

6. The method according to claim 1, wherein the composition comprises a food or beverage comprising the non-digestible oligosaccharide and at least one cereal, vegetable, fruit, animal milk, or animal protein.

7. The method according to claim 1, wherein a human baby, infant, toddler, or young child is a weaning infant or a weaning toddler.

8. The method according to claim 7, wherein the toddler is between 12 to 36 months of age.

9. The method according to claim 1, wherein said condition is selected from mycotoxicoses, listlessness, inactivity, fatigue, chills, dizziness, headache, nausea, sore throat, coughing, vomiting, reduced food or feed intake, slowed weight gain, food or feed refusal, weight loss, diarrhoea, blood in the stool, rectal haemorrhaging, gastrointestinal tract necrosis, bone marrow necrosis, destruction of bone marrow, lymphoid tissue necrosis, severe dermal necrosis, changes in blood parameters, modulation of serum immunoglobulin levels, abdominal pain, throat irritation, gastrointestinal disturbances, gastrointestinal inflammation, dermal irritation, abortion, anaemia, leukopenia, cytotoxicity, immunosuppression, necrotic lesions in mouth parts, erosion of mucosal epithelium of the stomach, erosion of mucosal epithelium of the small intestine, haemorrhage, severe gastroenteritis, death, massive haemorrhaging in the small intestine, pathological degeneration of bone marrow cells, pathological degeneration of lymph node cells, pathological degeneration of intestine cells, inhibition of DNA synthesis, inhibition of protein synthesis and alimentary toxic aleukia (ATA).

10. A method of treating or alleviating a trichothecene mycotoxin exposure associated condition in a human baby, infant, toddler, or young child suffering from same, comprising exposing a cell, tissue or organ of the human baby, infant, toddler, or young child to a composition comprising a non-digestible oligosaccharide having a degree of polymerisation (DP) of 2-10.

11. The method according to claim 10, wherein the trichothecene mycotoxin comprises deoxynivalenol.

12. The method according to claim 10, wherein the non-digestible oligosaccharide comprises a galactooligosaccharide and/or a fructooligosaccharide.

13. The method according to claim 12, wherein the non-digestible oligosaccharide comprises a transgalacto-oligosaccharide.

14. The method according to claim 13, wherein the non-digestible oligosaccharide composition comprises a galacto-oligosaccharide (GOS).

15. The method according to claim 10, wherein the cell, tissue or organ is exposed to the composition ex-vivo.

16. The method according to claim 10, wherein the condition is selected from mycotoxicoses, listlessness, inactivity, fatigue, chills, dizziness, headache, nausea, sore throat, coughing, vomiting, reduced food or feed intake, slowed weight gain, food or feed refusal, weight loss, diarrhoea, blood in the stool, rectal haemorrhaging, gastrointestinal tract necrosis, bone marrow necrosis, destruction of bone marrow, lymphoid tissue necrosis, severe dermal necrosis, changes in blood parameters, modulation of serum immunoglobulin levels, abdominal pain, throat irritation, gastrointestinal disturbances, gastrointestinal inflammation, dermal irritation, abortion, anaemia, leukopenia, cytotoxicity, immunosuppression, necrotic lesions in mouth parts, erosion of mucosal epithelium of the stomach, erosion of mucosal epithelium of the small intestine, haemorrhage, severe gastroenteritis, death, massive haemorrhaging in the small intestine, pathological degeneration of bone marrow cells, pathological degeneration of lymph node cells, pathological degeneration of intestine cells, inhibition of DNA synthesis, inhibition of protein synthesis and alimentary toxic aleukia (ATA).

17. The method according to claim 1 wherein the composition is an infant formula or growing up milk.

18. The method according to claim 10 wherein the composition is an infant formula or growing up milk.

\* \* \* \* \*